United States Patent [19]

Clemens

[11] Patent Number: 4,633,013

[45] Date of Patent: Dec. 30, 1986

[54] PREPARATION OF α-HALOACETOACETIC ESTERS

[75] Inventor: Robert J. Clemens, Kingsport, Tenn.

[73] Assignee: Eastman Kodak Company, Rochester, N.Y.

[21] Appl. No.: 619,450

[22] Filed: Jun. 11, 1984

[51] Int. Cl.$^4$ .................... C07C 67/00; C07C 67/333; C07C 67/716; C07C 67/732
[52] U.S. Cl. ....................................... 560/174; 560/17; 560/23; 560/43; 560/51; 560/60; 560/183; 560/184; 260/408; 558/178; 558/179
[58] Field of Search ................... 560/184, 60, 174, 51, 560/43, 23, 17, 183; 260/408

[56] References Cited

PUBLICATIONS

Boese, A. B., *Ind. Eng. Chem.* 32, 16 (1940).
Chick et al., *J. Am. Chem. Soc.* 93, 946 (1908).
Chick et al., *J. Am. Chem. Soc.* 97, 1978 (1910).
Boehme, *Org. Syn. Coll.*, vol. 4, 590 (1963).
Blomquist et al., *J. Am. Chem. Soc.*, vol. 70, p. 29 (1948).

*Primary Examiner*—Werren B. Lone
*Attorney, Agent, or Firm*—John F. Stevens; Clyde L. Tootle; Gary C. Bailey

[57] ABSTRACT

Disclosed is a process for the preparation of α-haloacetoacetic esters by the reaction of an alkali metal alkoxide with a 5-halo-4H-1,3-dioxin-4-one compound, the desired product being obtained as an alkali metal salt which may be converted to the corresponding free ester by treating with acid.

5 Claims, No Drawings

PREPARATION OF α-HALOACETOACETIC ESTERS

BACKGROUND OF THE INVENTION

This invention relates to a novel process for the preparation of α-haloacetoacetic esters by the reaction of an alkali metal alkoxide with a 5-halo-4H-1,3-dioxin-4-one compound.

The preparation of acetoacetic esters by the reaction of alcohols and diketene in the presence of an acid catalyst has been described by A. B. Boese in *Ind. Eng. Chem.* 32, 16 (1940). The sodium enolate salt of ethyl acetoacetate has been reported by Chick et al, *Journal of American Chemical Society* 93, 946 (1908) and 97, 1978 (1910) to be produced by reacting diketene and sodium ethoxide in dry alcohol. The desired α-halogenated product may be obtained by treating the acetoacetic ester with a suitable halogenating agent, e.g. $SO_2Cl_2$. [See Boehme, *Org. Syn. Coll.*, Vol. 4, 590 (1963)].

Reported by Blomquist et al in *Journal of American Chemical Society*, Vol. 70, page 29 (1948) is the preparation of ethyl 2-bromoacetoacetate by first treating ketene dimer in chloroform solution with N-bromosuccinimide followed by reaction with ethyl alcohol. The 2-chloro derivative was similarly prepared by treating ketene dimer with N,2,4-trichloroacetanilide followed by reaction with ethyl alcohol. Reported yields are 43% and 35%, respectively.

An alternate method has now been found for producing α-haloacetoacetic esters. According to this process, α-haloacetoacetic esters are obtained from 5-halo-4H-1,3-dioxin-4-ones by the reaction thereof with an alkali metal alkoxide.

By this process various α-haloacetoacetic esters may be obtained using a common starting material. The product is advantageously obtained as an enolate salt which affords protection of the halogen from displacement. In addition, the 5-halo precursor is obtained without the use of expensive halogenating agents. The process is particularly advantageous for halogen-sensitive alcohols since the halogen moiety is introduced prior to ring opening of the dioxinone compound. While 1,3-dioxin-4-one compounds such as 2,2,6-trimethyl-4H-1,3-dioxin-4-one are known to react in a manner similar to diketene in many reactions, reacting sodium ethoxide with the aforementioned dioxinone does not give ethyl acetoacetate. Surprisingly 4H-1,3-dioxin-4-one compounds which contain Cl or Br at the 5-position of the dioxinone ring do react with alkali metal alkoxides to give acetoacetic esters monohalogenated at the α-position.

SUMMARY OF THE INVENTION

The present invention concerns the preparation of α-haloacetoacetic esters. According to the process of this invention an alkali metal alkoxide is reacted with a 5-halo-4H-1,3-dioxin-4-one compound at a temperature of about −40° C. to about 50° C. to give an α-haloacetoacetic ester. The α-haloacetoacetic esters obtained by this process are useful intermediates for synthesizing a wide variety of compounds including, for example, pharmaceuticals and dye intermediates as described in U.S. Pat. No. 3,876,647 (1975); *J. Am. Chem. Soc.* 57, 1876 (1935); *J. Org. Chem.* 43, 3821 (1978); and *Chem. Ber.* 88, 130 (1955).

DETAILED DESCRIPTION OF THE INVENTION

The invention described herein relates to the preparation of α-haloacetoacetic esters. The process of this invention comprises reacting an alkali metal alkoxide with a 5-halo-4H-1,3-dioxin-4-one compound to obtain an α-haloacetoacetic ester. The process of the invention may be represented by the following reaction

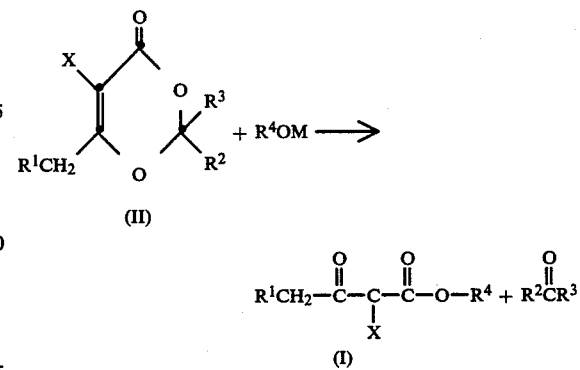

In the above formula X is Cl or Br; $R^1$ can be any substituent which is not reactive with the alkali metal alkoxide or does not otherwise interfere with the course of the reaction; $R^2$ and $R^3$, which are residues of the ketone from which the 4H-1,3-dioxin-4-one compounds are derived, can each independently be alkyl, aryl, substituted aryl, or collectively alkylene; $R^4$ can be alkyl or aralkyl; and M is an alkali metal ion.

Typical substituents for $R^1$ are hydrogen, Cl, Br, alkyl, alkoxy, aryl, substituted aryl, or a hetero moiety. The alkyl substituent generally may be saturated or unsaturated, and branched or straight chain having up to about 20 carbon atoms. The alkoxy substituent, which generally may have from 1–4 carbon atoms, includes, for example, methoxy and ethoxy. The aryl substituent generally is intended to mean phenyl and substituted aryl and includes, for example, p-nitrophenyl. Examples of the heteromoieties include phenylthio, anilino and diethyl phosphonato [i.e., $(CH_3CH_2O)_2PO$. The alkyl moieties of the disclosed substituents for $R^2$ and $R^3$ generally can be lower alkyl (i.e., $C_1$–$C_6$), either branched or straight chain. Examples of these include methyl, ethyl, propyl and isobutyl. The aryl substituent generally can be phenyl and the substituted aryl group may contain any substituent which is not reactive with the alkali metal alkoxide or does not otherwise interfere with the course of the reaction. Examples of substituted aryl groups include p-nitrophenyl and o-chlorophenyl. Examples of the alkylene groups are tetramethylene and pentamethylene [i.e., $-CH_2(CH_2)_2CH_2-$ and $-CH_2(CH_2)_3CH_2-$]. Most commonly and preferably $R^1$ and $R^2$ are each methyl.

The alkyl moieties of the alkyl and aralkyl substituents disclosed for $R^4$ are generally lower alkyl (i.e., $C_1$–$C_6$). Examples include methyl, ethyl, isopropyl, isobutyl, and benzyl. For most applications $R^4$ will be methyl or ethyl.

The alkali metal ion, represented by M in the above formula, may be sodium, lithium or potassium with sodium being preferred for reasons of economy. The mole ratio of alkali metal alkoxide to dioxene generally may be in the range of at least 1.0 up to about 2.0 with best results being obtained with a mole ratio of about 1.0 to about 1.2.

The temperature at which the process may be carried out may range from about −40° to about 50° C. with ambient temperatures, i.e., 0°–25° C., being preferred.

A solvent may be employed in this embodiment of the invention. Desirably, an alkanol solvent, one having the same number of carbon atoms as the alkali metal alkoxide, will be used. The amount of solvent used is not critical to the reaction and generally is dictated by economy and convenience.

The α-haloacetoacetic ester which is initially formed as an enolate salt can be reacted further to produce other derivatives or converted to the free ester by acidification.

The 5-halo starting material (II) is obtained by treating a 4H-1,3-dioxin-4-one with $X_2$ or $SO_2X_2$, wherein X is Cl or Br. Elemental chlorine and bromine are the preferred halogenating agents. The halogenating agent will generally be employed in stoichiometric amounts and preferably in slight excess, that is, up to about 1.2 moles per mole of (I).

The conditions of the halogenation may be varied considerably, depending on the halogenating agent used and whether the reaction is carried out in a gaseous or liquid phase. In carrying out the reaction using elemental chlorine or bromine and in a liquid phase, for example, the reaction is crried out at temperatures and pressure sufficient to maintain chlorine or bromine in liquid form, i.e., at atmospheric pressure the temperature for chlorine will be below −35° C. and below 59° C. for bromine. Of course, higher temperatures may be used with the use of elevated pressures.

In carrying out the reaction in a liquid phase a solvent is not required but one may be used if desired. Typical solvents which may be used are, for example, aliphatic or aromatic hydrocarbons, or chlorinated aliphatic or aromatic hydrocarbons, including, for example, methylene chloride, chloroform, xylene, chlorobenzene and the like. The amount of solvent generally will be dictated by economy and convenience. A by-product of the halogenation reaction is a hydrogen halide. This by-product generally may be removed by addition of a base to the product mixture such as an amine or carbonate salt, including, for example, pyridine triethylamine, or sodium carbonate.

The 1,3-dioxin-4-one from which the 5-halo starting material (II) is obtained can be prepared according to the procedures described in the *Chem. Pharm. Bull.* 31, 1896 (1983); *Liebigs Annalen der Chemie* 1953 (1982); *Journal of American Chemistry Society*, 74, 6305 (1952) and 75, 5400 (1953) or by procedures analogous thereto.

In a preferred embodiment of this invention, compound (II) is 5-chloro-2,2,6-trimethyl-4H-1,3-dioxin-4-one and the alkali metal alkoxide is sodium methoxide.

The following examples are given to further illustrate the invention, but it is to be understood that the invention is not to be limited in any way by the details described therein.

EXAMPLE 1

Preparation of 5-Chloro-2,2,6-Trimethyl-4H-1,3-Dioxin-4-one

A solution of 2,2,6-trimethyl-4H-1,3-dioxin-4-one (0.2 mol, 28.4 g) in 100 ml of $CH_2Cl_2$ was cooled to −50° C. and liquid chlorine (0.25 mol) was added dropwise over five minutes. The solution was allowed to warm to 20° C. over 30 minutes, and the solvent was then removed in vacuo, leaving 35.8 g (100% yield, 92% assay) of a pale yellow oil. A portion of this mixture was purified by flash chromatography (10% $Et_2O$/hexanes on silica) to provide the title compound as white crystals.

EXAMPLE 2

Preparation of Methyl-α-Chloroacetoacetate

A solution of 25% sodium methoxide in methanol (5 ml, 21.6 mmol) was added to a solution of 5-chloro-2,2,6-trimethyl-4H-1,3-dioxin-4-one (3.24 g, 18.4 mmol) in 10 ml of methanol at 20° C. The resulting yellow solution was stirred for 10 minutes, acidified with 10% HCl, and extracted with ether. Evaporation of the ether provided 2.35 g (94% yield, NMR assay ~90%) of a pale yellow oil, which was distilled to provide 1.8 g (66%) of pure title compound as a colorless liquid.

EXAMPLE 3

Preparation of Ethyl-α-Chloroacetoacetate

Sodium metal (0.3 g, 12 mmol) was added to 10 ml of ethanol, and then 5-chloro-2,2,6-trimethyl-4H-1,3-dioxin-4-one (1.76 g, 10 mmol) was added. The reaction was stirred one hour at 20° C., during which time the sodium dissolved. The reaction partitioned between ether and saturated ammonium chloride which had been acidified to pH ~2 with HCl. Evaporation of the ethereal layer, followed by distillation afforded 1.15 g (70%) of the title compound as a colorless liquid.

EXAMPLE 4

Preparation of Ethyl-α-Bromoacetoacetate

Sodium metal (13.7 g, 0.59 mmol) was dissolved in 500 ml of absolute ethanol, and the resulting ethoxide solution was cooled to 0° C. Crude 5-bromo-2,2,6-trimethyl-4H-1,3-dioxin-4-one (115.5 g, 0.5 mmole at 95% purity) was then added, dropwise, to the chilled ethoxide solution over 30 minutes and the dark orange reaction mixture was stirred an additional 30 minutes at 0° C. The reaction was poured into 500 ml of ether and 550 ml of 1N HCl, and the organic layer was washed repeatedly with water (4×250 ml) and then dried over $Na_2SO_4$. Removal of solvent in vacuo (30° C., 2 Torr), followed by distillation on a 2-inch wiped-film molecular still (120° C. jacket, 0.2 Torr) afforded 68.7 g (71%) of a pale yellow oil (98% pure by gc).

The invention has been described in detail with particular reference to preferred embodiments thereof, but it will be understood that variations and modifications can be effected within the spirit and scope of the invention.

I claim:

1. A process for the preparation of an alkali metal salt of an α-haloacetoacetic ester comprising reacting an alkali metal alkoxide with a substituted 5-halo-4H-1,3-dioxin-4-one having the formula:

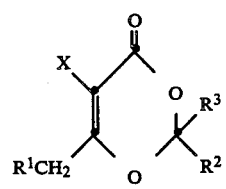

wherein $R^1$ is hydrogen, chloro, bromo, alkyl having 1 to 20 carbon atoms, alkoxy having 1 to 4 carbon atoms, phenyl, p-nitrophenyl or a heteromoiety selected from the group consisting of phenylthio and anilino; $R^2$ and $R^3$ are alkyl groups containing 1 to 6 carbon atoms, phenyl, p-nitrophenyl, o-chlorophenyl and collectively an alkylene group and X is a chloro or bromo group at a temperature of about $-40°$ C. to about $50°$ C.

2. The process of claim 1 wherein the alkali metal alkoxide is sodium methoxide or sodium ethoxide.

3. The process of claim 2 wherein the mole ratio of the alkali metal alkoxide to substituted 5-halo-4H-1,3-dioxin-4-one compound is about 1.0 to about 2.0.

4. The process of claim 3 comprising reacting said alkali metal alkoxide with 5-halo-2,2,6-trimethyl-4H-1,3-dioxin-4-one.

5. A process which comprises
 (a) preparing an alkali metal salt of an α-haloacetoacetic ester by reacting (I) sodium methoxide or sodium ethoxide with (II) 5-chloro-2,2,6-trimethyl-4H-1,3-dioxin-4-one or 5-bromo-2,2,6-trimethyl-4H-1,3-dioxin-4-one at a temperature of about $-40°$ C. to about $50°$ C. wherein the mole ratio of I to II is about 1.0 to about 2.0, and
 (b) converting the salt of the α-haloacetoacetic ester to the free ester compound by treating with acid.

* * * * *